United States Patent [19]

Sitte et al.

[11] Patent Number: 4,551,992
[45] Date of Patent: Nov. 12, 1985

[54] APPARATUS FOR COOLING A BIOLOGICAL OR MEDICAL SPECIMEN

[75] Inventors: Hellmuth Sitte, Siefeld; Heinrich Kleber, Vienna, both of Austria

[73] Assignee: C. Reichert Optische Werke, AG., Vienna, Austria

[21] Appl. No.: 651,400

[22] Filed: Sep. 17, 1984

[30] Foreign Application Priority Data

Sep. 9, 1983 [DE] Fed. Rep. of Germany ....... 3332586

[51] Int. Cl.⁴ .............................................. F25B 19/00
[52] U.S. Cl. .................................... 62/514 R; 62/383
[58] Field of Search .................. 62/64, 78, 383, 514 R

[56] References Cited

U.S. PATENT DOCUMENTS

| | | | |
|---|---|---|---|
| 2,737,779 | 3/1956 | Lawrence | 62/383 |
| 4,232,532 | 11/1980 | Marsh | 62/383 |
| 4,302,950 | 12/1981 | Sitte | 62/514 R |
| 4,388,814 | 6/1983 | Schilling | 62/78 |
| 4,459,823 | 7/1984 | Josephs et al. | 62/514 R |

Primary Examiner—Ronald C. Capossela
Attorney, Agent, or Firm—Alan H. Spencer; Stephen Raines; Gary M. Nath

[57] ABSTRACT

Apparatus for cooling a biological or medical specimen comprises a cooling bath, an injection device for injecting a specimen into cooling liquid in the bath at a velocity of between 5 and 15 m/sec, and a sleeve. The sleeve is movable between a lower position in the bath and an upper position for limiting the effects of splashing as a specimen enters the bath. The injection device comprises a closure plate for co-operating with the sleeve to further limit the effects of splashing. The sleeve is operatively associated with the injection device in a manner such that movement of a specimen carrier of the device towards the bath to immerse a specimen is initiated when the sleeve is moved from the lower position to the upper position.

10 Claims, 5 Drawing Figures

APPARATUS FOR COOLING A BIOLOGICAL OR MEDICAL SPECIMEN

BACKGROUND OF THE INVENTION

This invention relates to apparatus for cooling a biological or medical specimen and, in particular, to apparatus for cryogentic-fixation of a specimen for microscope inspection. Cryogenic-fixation of a specimen involves the injection of the specimen at a rapid velocity, suitably between 5 and 15 m/sec, into a cooling liquid which may, for example, be pre-cooled to −190° C.

Cooling baths containing liquids at temperatures between −100° C. and −190° C., and with volumes between 5 and 100 ml, are used for numerous specimen-preparation operations, particularly for the process of shock-freezing or "cryogenic-fixation" of small biological or medical specimen for subsequent microscopic examination. Suitable preparation of the specimen which has been introduced into the cooling liquid can be achieved only when as much heat as possible is abstracted from the surface of the specimen within the shortest possible time. This applies particularly for biological or medical specimens which have not been pre-treated, that is, specimens which have not been subjected to a preliminary fixation and/or freezing-protection treatment. For such specimens, the cooling rate alone determines whether artificial separation of the water-rich plasmatic phases takes place (separation would render meaningful microscopical examination impossible) or whether the specimen freezes to a true-to-life, glassy form ("vitrification" takes place at cooling rates greater than 10,000° C./sec).

The cooling rates which are required for vitrification are obtained only in an edge zone of the specimen, this zone having a depth of 30 um at the most. The depth of the perfectly vitrified edge zone is determined essentially by the temperature and the specific properties of the cooling medium, and by the velocity at which the specimen enters the cooling medium. Liquified propane which has been cooled to a temperature only slightly above its freezing point (−190° C.) offers the best known conditions for vitrification. Using this cooling medium, initial cooling rates of the order of 100,000° C./sec are obtained, but only if the specimen is injected into the liquid at velocities exceeding 5 m/sec.

The liquefaction, cooling, and storage of propane, under constant-temperature conditions, presents few problems. However, the injection of the specimen presents considerable problems and hazards. Since the specimen is injected in at a comparatively high velocity, up to 15 m/sec, a considerable quantity of the cooling liquid may splash out of the cooling bath. Typically, the total quantity of cryogen is kept below 100 ml in order to minimise the hazards associated with propane, i.e., fire, and the danger of explosion. The diameter of the specimen, and/or of the injector, typically exceeds 3 mm, and it is usually necessary that the specimen should travel a distance of 5 to 10 cm in order to achieve adequate cooling. While it is possible to use a non-flammable cooling media, such as halogenated hydrocarbons, (e.g. FREON 13, which has a boiling point of −185° C.), these provide a 20% lower cooling rate and other problems still remain. The splashing of the cooling liquid will cause severe burns if the liquid strikes the skin.

More than 90% of the cooling medium is often lost from the cooling bath when specimens are introduced at velocities greater than 10 m/sec, the specimens and specimen holders are of conventional diameter (approximately 3 to 5 mm), and the injectors are of conventional diameter (approximately 4 mm). Insufficient liquid usually remains in the cooling both to cool further specimens, even when the specimens are small, and the heat capacities of the specimen-holder and injection device are low. When a specimen and specimen holder is insufficiently cooled, the quantity of heat which remains in the interior of the specimen, and/or in the specimen holder/injector assembly, causes secondary heating of the surface of the specimen following the initial superficial cooling. Hence, an artifical separation of the initially perfectly vitrified surface occurs. In order to be able to enhance the quality of the cryofixation by means of greater injection velocities, as well as for safe operations, it is desirable to adopt precautions to prevent splashing of the cooling medium even when the injection velocities are comparatively high.

OBJECT OF THE INVENTION

It is an object of the invention to avoid the above-mentioned disadvantages; that is, to provide an arrangement which substantially prevents the cooling liquid from being expelled from a cooling bath even when the injection velocities exceed 5 m/sec.

BRIEF DESCRIPTION OF THE INVENTION

According to this invention, there is provided apparatus for cooling a biological or medical specimen, the apparatus comprising a cooling bath for containing a cooling liquid, an injector having a specimen carrier which is movable along an injection path for immersing a specimen mounted on the specimen carrier in cooling liquid in the bath. A sleeve is movable along a path aligned with the injection path, between a lower position disposed in the bath and an upper position in which the specimen carrier is positioned within the sleeve for immersing a specimen mounted thereon. The sleeve and the injection device cooperate when the sleeve is in the upper position so that cooling liquid splashed from the bath as a specimen is immersed strikes the sleeve or a baffle on the injection device to drain back into the bath.

The specimen is shielded by means of the sleeve as the specimen approaches the cooling bath, the sleeve being pre-cooled by immersion in the cooling bath. Any cooling medium, which is displaced from the bath as the injector and specimen and specimen holder enter and penetrate the cooling liquid, is directed back into the cooling bath by the injection device and sleeve. The cooling medium drains back into the bath, for the most part along the cold walls of the sleeve, to become available again for continuing the process of withdrawing heat from the specimen and the specimen holder, which process is known as "aftercooling." All the hazards which are normally associated with splashing of the cooling medium in the laboratory are eliminated.

In a preferred embodiment, the sleeve is in a close, sliding fit with the wall of the cooling bath.

A tool receiver is mounted on or is integral with the sleeve, whereby a tool can be used to manually move the sleeve. The injection device comprises a generally horizontal closure-plate, or baffle, which has a low thermal capacity and which closes off the sleeve when the sleeve is in the upper position so that cooling medium is directed back into the cooling bath by the baffle, even if it would otherwise have escape through the space between the specimen holder and sleeve. The cooling medium quickly refills the bath without a significant temperature increase, which would interfere with the operation. The thermal capacities of the components of the apparatus, relative to the thermal capacity of the cooling medium, are preferable such that the rise in temperature of the cooling medium caused by the antisplash arrangement does not exceed 30° C. (so that in the case of propane the temperature rises from −190° to −160° C.) The greater part of the cooling liquid thermal capacity remains available for cooling the specimen, the specimen holder, and the injector.

In one development of the invention, the sleeve is spring-biased towards the upper position, the apparatus comprising releasable catch means for holding the sleeve in the lower position.

Alternatively, the apparatus further comprises electrical or electromagnetic motor means for moving the sleeve between the lower and upper positions. These developments considerably reduce the time taken to lift the sleeve, so that the risk of premature cooling of the specimen by the cold sleeve wall is reduced. These developments also provide a simple and reliable means for triggering lifting of the sleeve.

Preferably, the injection device comprises trigger means which, when activated, triggers movement of the specimen carrier towards the cooling bath, and wherein the sleeve or a member moutned thereon is adapted to activate the trigger means during the course of or at the completion of movement of the sleeve from the lower to the upper position. By this means injection is triggered at the earliest possible moment so that the risk of preamture cooling of the specimen is further reduced. The cryogenic-fixation operation therefore does not depend upon the skill and practice of the operator. Furthermore, premature injection without antisplash protection is prevented.

Preferably, to facilitate entry of a liquefied cooling medium into the bath, the sleeve comprises upper and lower portions of reduced outer diameter whereby annular spaces are defined between the upper and lower portions and the inwardly facing surface of the bath when the sleeve is in the lower position, the sleeve further comprising one or more grooves extending between the upper and lower portions, and the lower portion defining an outlet from the lower annular space to the space defined by the sleeve, whereby cooling liquid can enter the space defined by the sleeve via the upper annular space, the grooves, the lower annular space and the outlet.

In order to enable liquid to be removed from a bath, the apparatus preferable further comprises a container for insertion into the cooling bath, the container comprising a valve adapted for opening to permit cooling liquid to enter the bath as the container is inserted into the bath and for closing to retain cooling liquid in the container when the container is removed from the bath.

BRIEF DESCRIPTION OF THE DRAWINGS

Illustrative embodiments of the invention are described in detail by reference to the accompanying drawings, wherein.

DETAILED DESCRIPTION OF THE DRAWINGS

Figure 1:
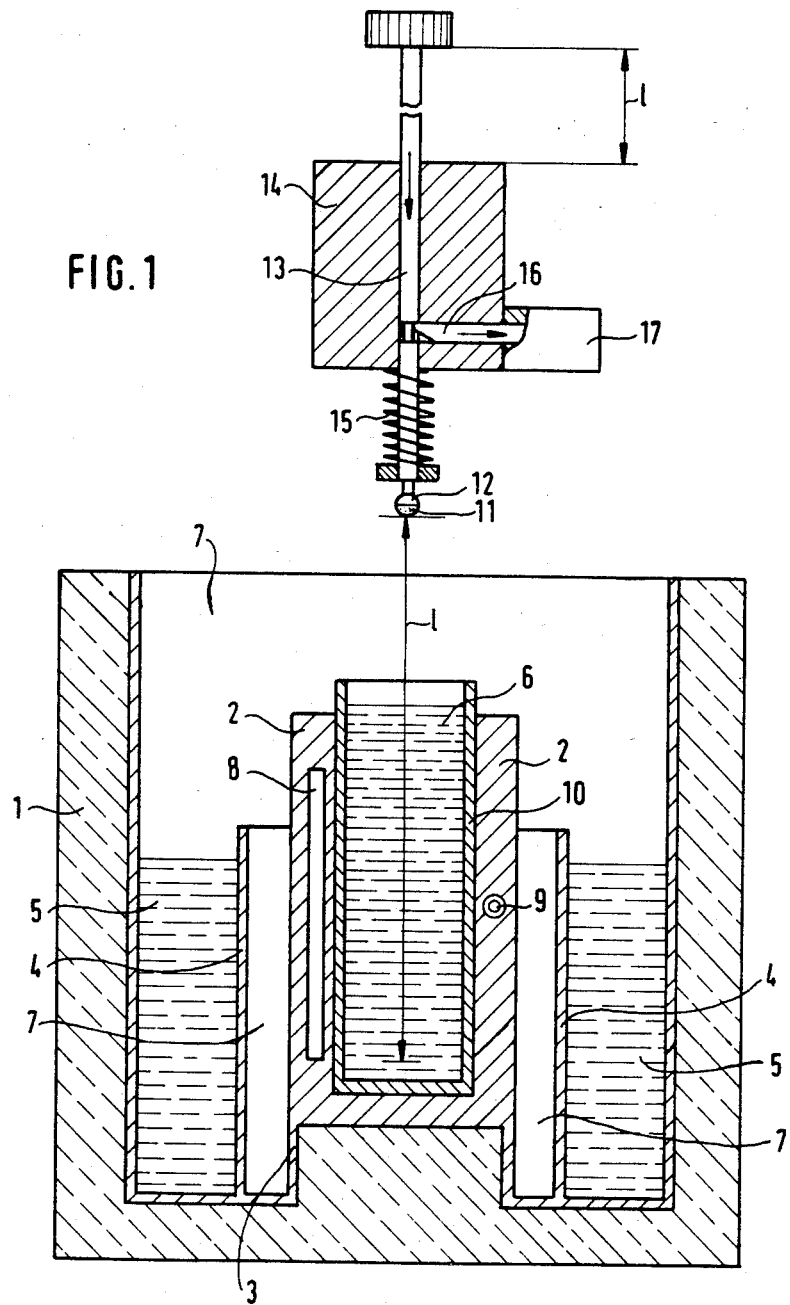
FIG. 1 shows, in cross-section, a diagrammatic side view of known cooling apparatus.

The apparatus which is illustrated in FIG. 1, corresponds to the present state of the art. A cylindrical metal cooling bath 2 is located in an insulating vessel 1, the cooling bath being connected to a cylindrical sleeve 4 via a thin-walled hollow sleeve 3, the sleeve 4 preventing direct contact between liquid nitrogen 5 which is used as the cryogen and the cooling bath during use of the apparatus. Liquefied propane or a halogenated hydrocarbon (e.g. FREON 13) is normally used as a cooling liquid 6.

The freezing points of cooling liquids of the above-mentioned types are higher than the boiling point of liquid nitrogen (the freezing point of propane is −190° C., that of FREON 13 is −185° C., and that of FREON 22 is −155° C.; and the boiling point of liquid nitrogen is −196° C.). Unless preventitive measures are taken, the liquid cools until frozen. The liquid would lose heat via the sleeve 3 and via cold nitrogen gas 7 which completely surrounds the cooling bath 2, being present as a result of continuous boiling of the liquid nitrogen in the vessel 1. such cooling is prevented by means of a heating cartridge 8, the heat output from which is, as a rule, controlled in a manner such that the temperature of the cooling bath 2, and hence that of the cooling liquid 6, in continuously and thermostatically held at a value slightly above the freezing point of the cooling liquid. The thermostatic control is achieved by means of a temperature sensor 9 and an electronic control circuit which is not illustrated.

The majority of cooling liquids are combustible and are also harmful to health so that it is necessary to prevent evaporation into atmosphere. To facilitate safe removal of the cooling liquid upon completion of the preparation of a specimen, a removable insert-sleeve 10 is located in the cylinder 2, for containing the cooling liquid.

As shown in FIG. 1, a specimen 11 is located on a carrier 12 which is suitable for subsequent operations such as cryogenic-ultramicrotoming, freeze-etching cryogenic-substitution, and freeze-drying. The carrier is mounted on an injection rod 13. The rod is slidably movable in a cylindrical hole in the guide 14.

To achieve high cooling rates when injecting a specimen, the injection rod 13 is accelerated by a compression spring 15 (the velocity which can be attained by free fall of the specimen is too low for normal requirements). The injection operation is triggered by pulling a bolt 16 back, in the direction of the arrow, either manually, or by means of a triggering device 17 which is actuated by electrical or electromagnetic means. following triggering, the specimen 1 travels over a distance "L" of approximately 100 mm, in the course of which it enters the liquid 6 at a velocity of between 5 and 15 m/sec. A major disadvantage of apparatus of this type is the splashing caused by the immersion of specimens in the cooling liquid.

Figure 2:
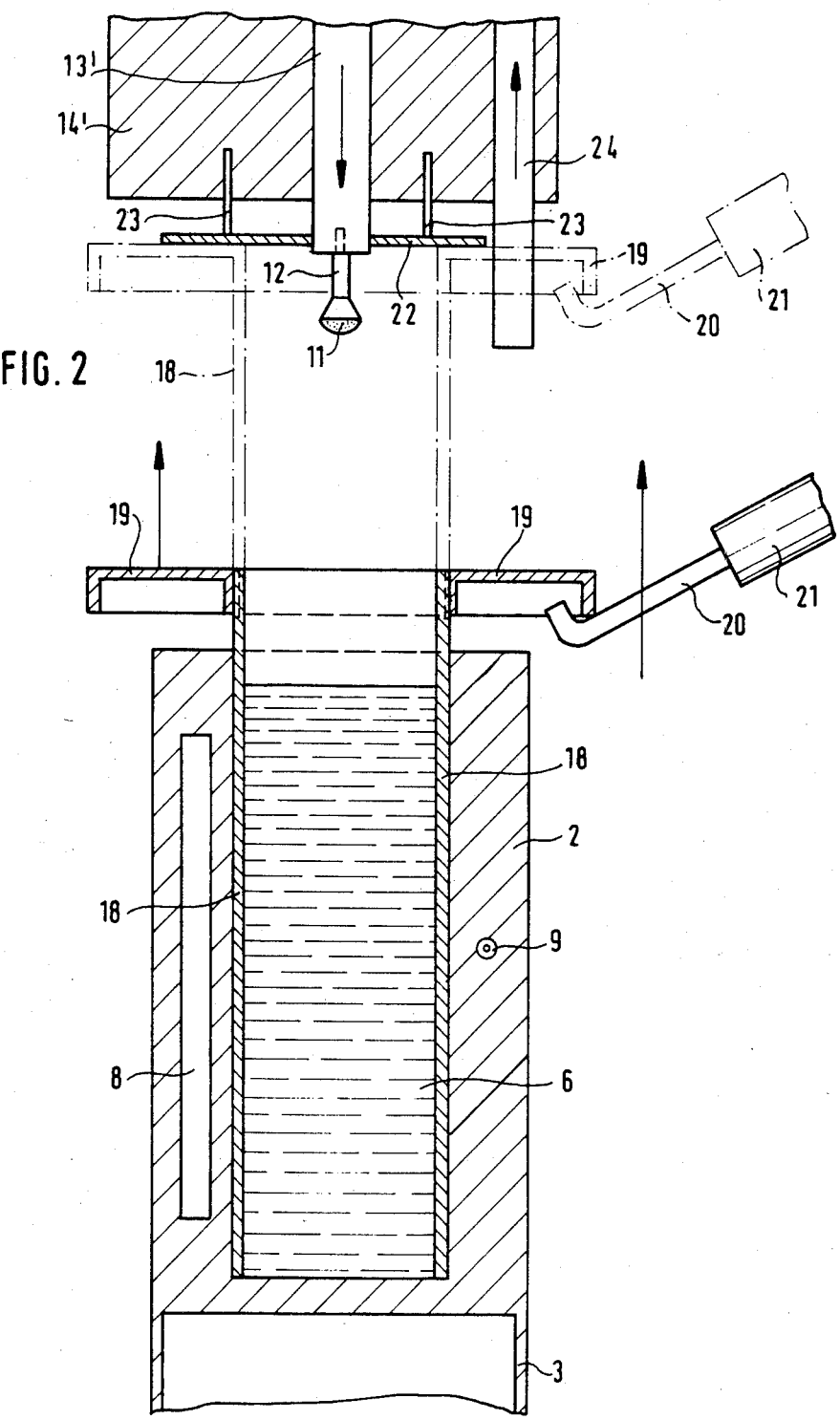
FIG. 2 is a diagrammatic across-sectional representation of a first embodiment of apparatus according to the invention.

The apparatus shown in FIG. 2 comprises a cylindrical sleeve 18 which replaces the insert-sleeve 10 illustrated in FIG. 1. A tool-receiving closure member 19 is secured to an upper rim of the cylindrical sleeve, the closure member being adapted to receive a suitable tool 20 with an insulating handle 21 to enable the sleeve to be lifted. The dimensions of the sleeve are such that the sleeve is a close sliding fit in the cylindrical bore of the cooling bath 2, to facilitate lifting of the sleeve.

The cylindrical sleeve 18 can be lifted until the sleeve engages a thin plate 22, which is secured by means of bolts 23 to a guide 14' of an injection device. The plate comprises an aperture for permitting through-passage of the injector rod 13'. The raised sleeve (represented by broken lines), and the plate provide an antisplash enclosure which directs virtually all splashing cooling liquid back into the cooling bath 2. Prior to being lifted the sleeve and closure member are cooled to the temperature of the cooling bath. Furthermore the thermal capacity of the plate 22 is low, and the plate is spaced from the guide to minimise thermal contact. Consequently the antisplash enclosure does not cause any significant heating of the cooling liquid before the liquid draws back into the bath. Heating caused by the components of the antisplash enclosure is negligible, invariably remaining below 30° C. and given suitable conditions remaining below 5° C.

Injection of the specimen 11 is triggered by moving a bolt 24 upwardly, in the arrowed direction, the bolt being moved upon engagement with the closure membe 19 when the sleeve is raised. It will be appreciated that the bolt can be moved in various ways, for example, by means of mechanical intermediate elements, or by electrical or electromagnetic means. Accidental triggering which could occur (for example by pushing in the bolt 24 while attaching the specimen 11, or the specimen carrier 12, to the injector rod 13') can be prevented by means of an additional unlocking device which is operated manually.

When the apparatus is in use and the protective sleeve 18 has been lifted, the injection operation takes place immediately, so that damage to the specimen 11, which can occur when the specimen remains in close proximity to the refrigerated sleeve, is minimised. The operative connection between the lifting of the protective sleeve and the triggering of the injection operation in conjunction with the additional locking mechanism, ensures that injection does not take place until the sleeve is raised.

Figure 3:
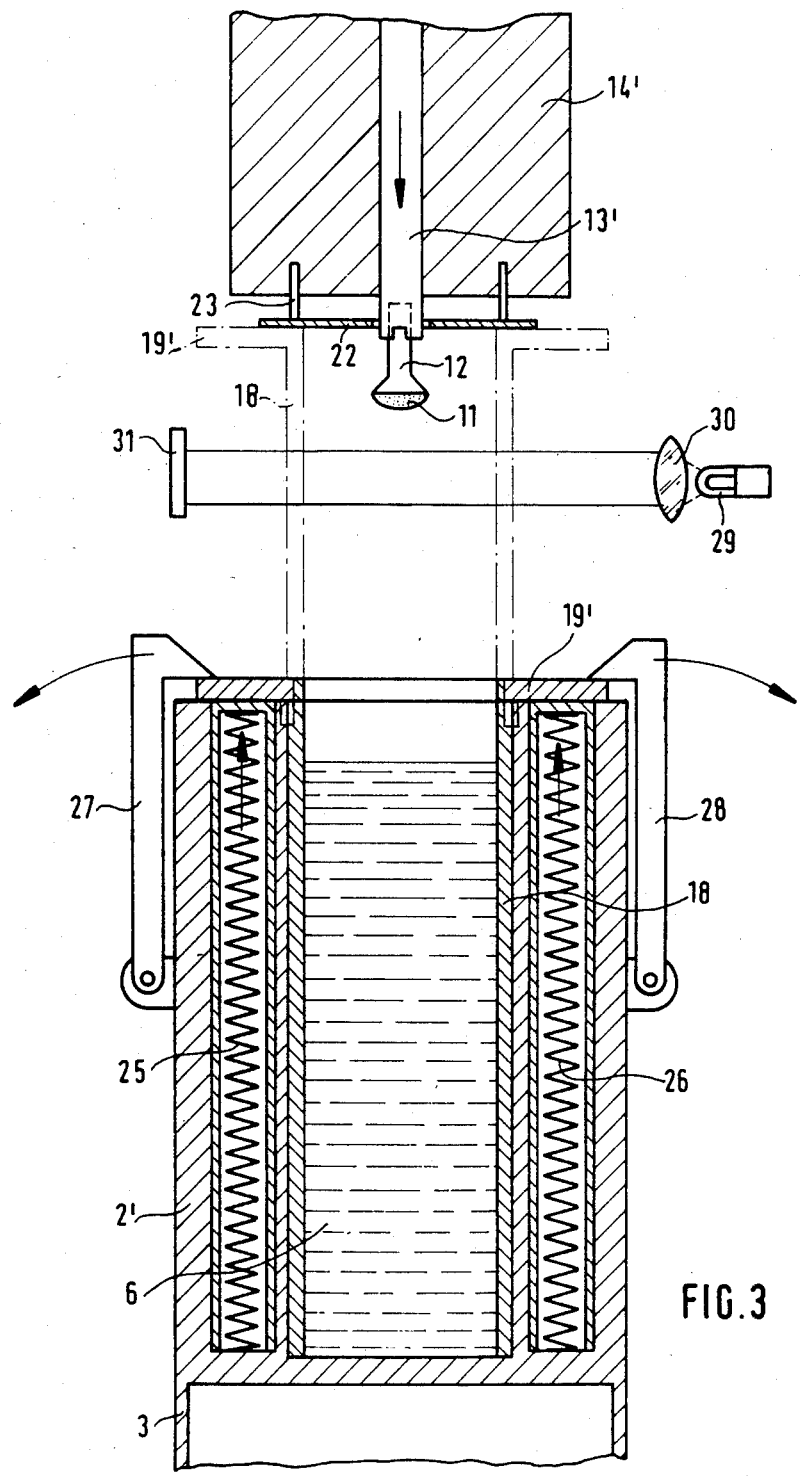
FIG. 3 is a diagrammatic sectional representation of a second embodiment of apparatus according to the invention.

In the embodiment of apparatus shown in FIG. 3, the sleeve 18 is lifted by means of compression springs 25 and 26, the springs being released upon movement of triggering elements 27 and 28. Injection of the specimen 11 is triggered when the sleeve interrupts a light beam, light from a source 29 being focused by a lens 30 on a photosensitive device 31. Downward movement of the specimen carrier can be commenced either during upward movement of the sleeve, or after an appropriate delay. As a result of the movement in opposite directions of the sleeve and the specimen carrier, the duration of the operation is minimised, and the effect of premature low temperatures on the specimen is reduced to a minimum.

Figure 4:
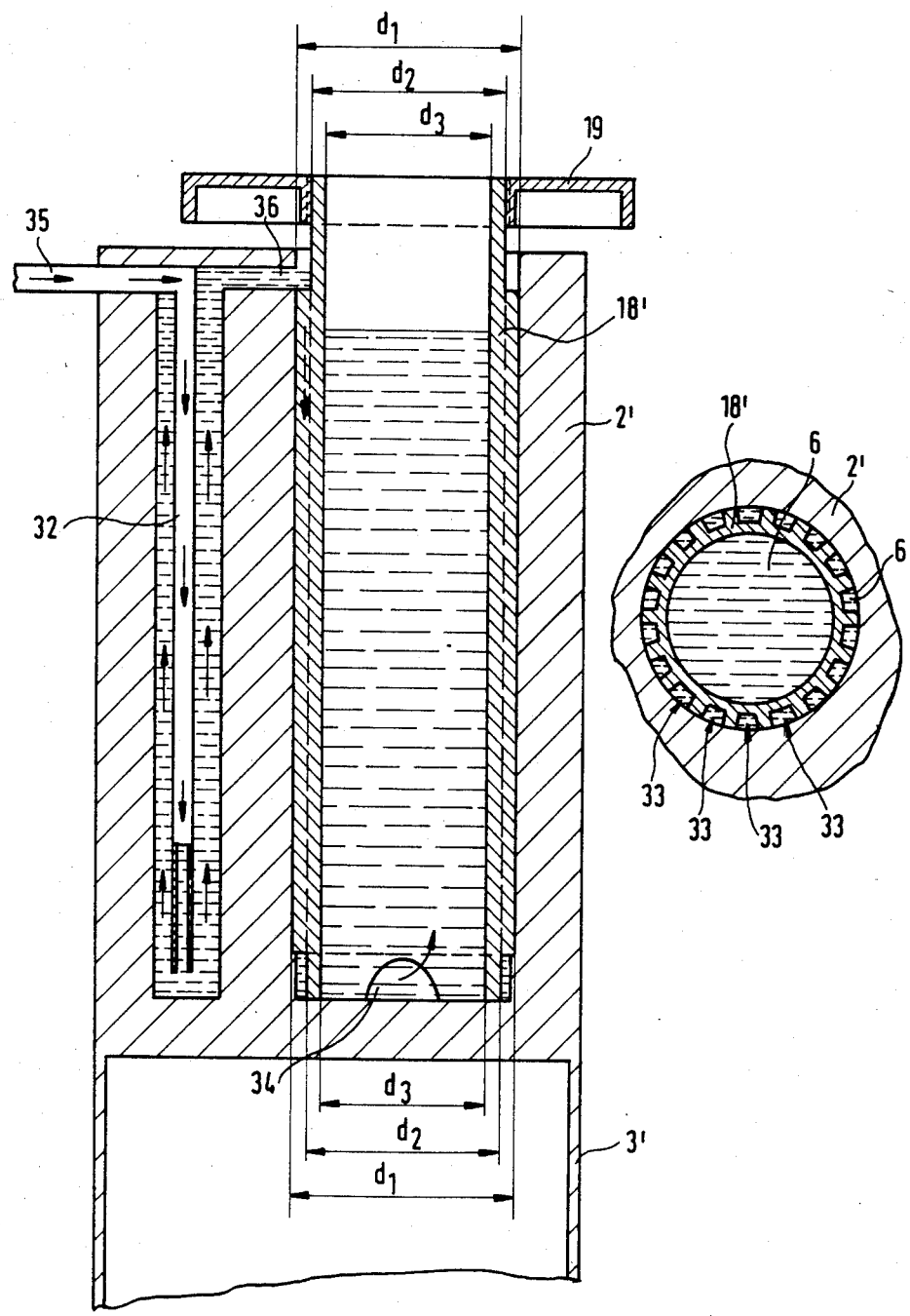
FIG. 4 is a diagrammatic sectional representation of a third embodiment of apparatus according to the invention.

In the embodiment of the apparatus shown in FIG. 4, the sleeve 18' is a close sliding fit in the cooling bath but has upper and lower end portions of reduced diameter outer "$d_2$". The diameter of the end portions differs from the diameter "$d_1$" of the cooling bath by an amount which is sufficient to enable the cooling liquid to move in the annular spaces between the cylindrical wall of the cooling bath and the outwardly facing surfaces of the end portions of the sleeve. Grooves 33 in the outwardly facing surface of the sleeve extend generally vertically to enable the cooling liquid to flow downwardly between the upper and lower end portions. An outlet into the space defined by the sleeve from the space between the lower end portion of the sleeve and the wall of the cooling bath is provided by one or more cutouts 34 at the lower end of the sleeve. The cooling medium can be liquefied without removing the sleeve 18', the risk of overpressure, caused by blocking of the downward flow during an attempt to achieve liquefaction being eliminated. A gas (for example propane or FREON gas) enters liquefier 32 through tube-connection 35, the liquefied medium entering the cooling bath through the outlet 36. In the cooling bath, the liquid flows downwardly along the grooves 33 and fills the cooling bath from below, through the cutouts 34.

Figure 5:
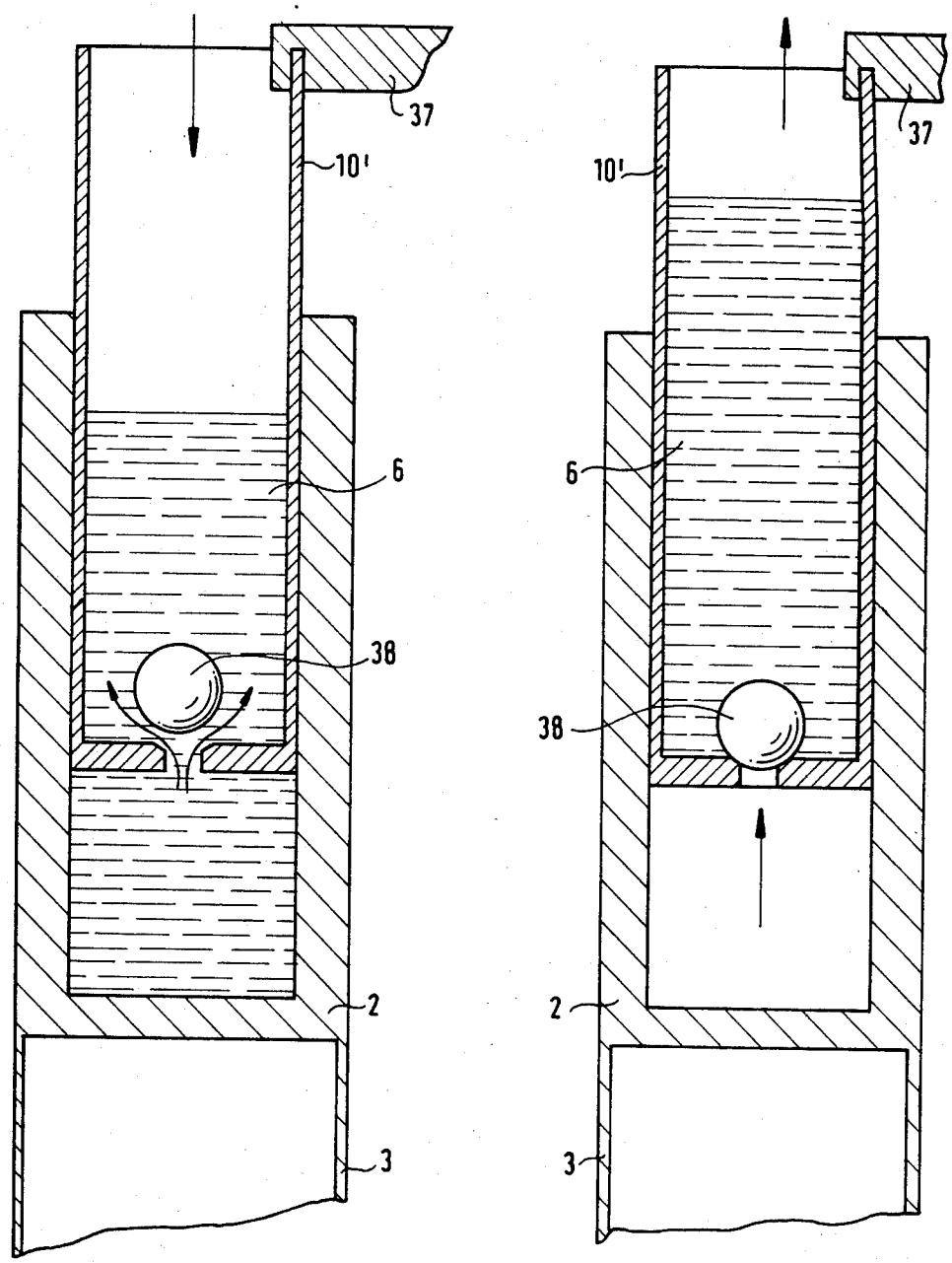
FIG. 5 is a diagrammatic sectional representation of a fourth embodiment of apparatus according to the invention.

The apparatus shown in FIG. 5 is adapted to facilitate disposal of the cooling liquid. The sleeve is removed from the cooling bath 2 following completion of the specimen preparation procedure. In its place, a container 10' which comprises a ball valve is inserted, in the direction indicated in the left hand sectional diagram, using a suitable tool 37. A ball 38 is spaced from an aperture in the base of the container as the container is inserted to enable cooling liquid 6 to enter the container. Once the container has been fully inserted into the cooling bath, the container is raised, the ball blocking the aperture so that the cooling liquid is retained in the container. The ball valve can comprise a compression spring to facilitate operation thereof. The container enables cooling liquid to be transferred into a pressure vessel which is suitable for storing combustible media, or to be reused or to be flared off in a known manner.

It will be appreciated that various combinations and modifications of features of the embodiments which have been described by reference to FIGS. 2 to 5 can be made which are within the scope of the invention. The sleeve may, for example, be other than cylindrically shaped. Instead of the grooves 33 in the sleeve 8' illustrated in FIG. 4, the through-flow of the liquefied cooling medium can be provided for by means of recesses in the wall of the cooling bath 2'. the cooling liquid removal sleeve 10' can be dimensioned for introduction into the bath without removing the sleeve.

We claim:

1. An apparatus for cooling a biological specimen comprising:
   (1) an insulated containment vessel for containing a cryogenic fluid;
   (2) a bath for containing a cooling liquid positioned within said vessel, said bath having an open top;
   (3) means for cooling the cooling liquid utilizing the cryogenic fluid;
   (4) an injection rod positioned above said bath, said injection rod having a specimen carrier rigidly mounted thereon;
   (5) means for injecting said injection rod axially into said bath from a first upper position above the bath to a second lower position within the liquid; and
   (6) guard means to contain liquid splashed by the injection of the specimen carrier into the liquid whereby cooling liquid is substantially prevented from being thrown out of the cooling bath as a result of said splashing.

2. The apparatus according to claim 1 wherein said bath includes an open-ended sleeve inserted within said bath.

3. The apparatus according to claim 2 wherein said sleeve is cylindrical.

4. The apparatus according to claim 2 wherein said sleeve is close fitting and slideably mounted within said bath for movement between a first position substantially within said bath and a second position, said second position being in close proximity to said injection rod when said rod is in its first upper position.

5. The apparatus according to claim 4 wherein said sleeve is spring biased toward said second position, a releasably engaged catch means holding said sleeve in said first position.

6. The apparatus according to claim 4 wherein said sleeve is adapted with an outwardly extended flange rigidly mounted to the top of said sleeve.

7. The apparatus according to claim 4 wherein a tool-receiving member is mounted on or integral with the sleeve, whereby a tool can be used to manually effect movement of the sleeve.

8. The apparatus according to claim 4 wherein the injection means comprises trigger means which, when activated, triggers movement of the injection rod towards the cooling bath, and wherein the sleeve or a member mounted thereon is adapted to activate the trigger means during the course of or at the completion of movement of the sleeve from its lower position to its upper position.

9. The apparatus according to claim 4 wherein said sleeve is electromechanically moved from its first lower position to its second upper position.

10. The apparatus according to claim 4 wherein the sleeve comprises upper and lower portions of reduced outer diameter whereby annular spaces are defined between the upper and lower portions and the inwardly facing surface of the bath when the sleeve is in its lower position, said sleeve having at least one groove extending axially between the upper and lower portions, the lower portion defing an outlet from the lower annular space to the space defined by the sleeve, whereby cooling liquid can enter the space defined by the sleeve via the upper annular space, the groove, the lower annular space and the outlet.

* * * * *